United States Patent
Chang et al.

(10) Patent No.: US 7,097,810 B2
(45) Date of Patent: Aug. 29, 2006

(54) DELIVERY OF METERED AMOUNTS OF LIQUID MATERIALS

(75) Inventors: Timothy Chang, Montville, NJ (US); Peter Tolias, Westfield, NJ (US)

(73) Assignees: The Public Health Research Institute of the City of New York, Inc., Newark, NJ (US); New Jersey Institute of Technology, Newark, NJ (US)

( * ) Notice: Subject to any disclaimer, the term of this patent is extended or adjusted under 35 U.S.C. 154(b) by 575 days.

(21) Appl. No.: 10/184,502

(22) Filed: Jun. 26, 2002

(65) Prior Publication Data

US 2004/0002164 A1 Jan. 1, 2004

(51) Int. Cl.
*B01L 3/02* (2006.01)

(52) U.S. Cl. ............ 422/100; 436/180; 141/94; 347/27; 347/85; 347/86; 347/87

(58) Field of Classification Search ........... 422/100; 436/180; 141/94; 347/27, 85–87
See application file for complete search history.

(56) References Cited

U.S. PATENT DOCUMENTS

| 3,877,310 | A | * | 4/1975 | Pecsar et al. ............ 73/864.21 |
|---|---|---|---|---|
| 5,359,413 | A | | 10/1994 | Chang et al. |
| 5,686,777 | A | | 11/1997 | Chang |
| 5,981,733 | A | | 11/1999 | Gamble et al. |
| 5,990,587 | A | | 11/1999 | Shimanovich et al. |
| 6,024,925 | A | | 2/2000 | Little et al. |
| 6,063,339 | A | | 5/2000 | Tisone et al. |
| 6,359,370 | B1 | | 3/2002 | Chang |
| 6,387,330 | B1 | * | 5/2002 | Bova et al. ............ 422/100 |
| 6,722,395 | B1 | * | 4/2004 | Overbeck et al. ......... 141/1 |
| 2001/0051334 | A1 | | 12/2001 | Barth et al. |

OTHER PUBLICATIONS

Chang, T.N. and Davison, E.G., "Decentralized Controller Design Using Parameter Optimization Methods," C-TAT, vol. 2, No. 288, pp. 131-154 (1986), no month.
Chang, T.N., Kwadzogah, R., Caudill, R., "Vibration Control of Linear Robots Using Piezoelectric Actuators," Proceedings of the 2000 American Control Conference, Chicago, IL, Jun. 28-30, 2000 pp. 2523-2527.

* cited by examiner

Primary Examiner—Jan M. Ludlow
(74) Attorney, Agent, or Firm—Fish & Richardson P.C.

(57) ABSTRACT

Techniques for the delivery of metered amounts of liquid material include the use of a pin, such as an optical fiber. A sample of the liquid material may be placed on the tip of the pin for delivery to a target area, such as a specific location on a microarray, in a contactless manner. Light transmitted through the pin may be detected to facilitate accurate measuring of the pin's position.

43 Claims, 14 Drawing Sheets

| Process Table | |
|---|---|
| Time Entry | Light Intensity Entry |
| T=0 | =0 Volts |
| ⋮ | ⋮ |
| T=1 msec | =0.5 Volts |
| ⋮ | ⋮ |
| T=5 msec | =5 Volts |
| ⋮ | ⋮ |
| T=6 msec | =4 Volts |
| ⋮ | ⋮ |
| T=7 msec | =2.5 Volts |

FIG. 4

DELIVERY OF METERED AMOUNTS OF LIQUID MATERIALS

TECHNICAL FIELD

This disclosure relates to delivery of metered amounts of liquid materials.

BACKGROUND

Precision delivery methods for fabrication of microarrays, including DNA and other nucleic acid microarrays, antibody and other protein microarrays and the like, utilize one of two different approaches. One approach, represented by the Gene Chip processing of Affymetrix, utilizes photochemical processing adapted from semiconductor technology. Wafer masking techniques are used for serial deposition of desired reagents at predetermined locations on a surface. Due to the spatial specificity of the manufacturing process, photochemical processing has a high degree of accuracy and reproducibility. However, the process tends to be both inflexible and expensive, making it not useful for innovative, small-scale laboratory research purposes.

The other approach is printing, either impact printing or inkjet printing. While potentially offering flexibility and low cost, printing has serious drawbacks. For both impact and inkjet printing, minimum spot size and reliability are limitations. Only about 40,000 individual spots can be printed on a standard microscope slide, for example, with a spot size of 150 microns. Also, printing techniques tend to waste a large portion of material, generally more than seventy-five percent of the starting material. Further, impact printing requires frequent replacement of hollow pins which are used to draw up liquid and "print" the liquid on a slide.

SUMMARY

In one aspect, a liquid delivery apparatus is disclosed having a housing including a bore and a pin that includes a tip that is movably disposed within the bore. A reservoir having a port with an opening is adjacent to a side of the bore. The reservoir is for holding a liquid material for delivery to the opening of the pin. A first actuator is coupled to the reservoir to dispense a metered amount of the liquid material from the reservoir to the opening. A second actuator is coupled to the pin to provide controlled movement of the pin within the bore, such that during operation the dispensed liquid material adheres to the tip of the pin as the tip passes the opening. The second actuator provides for controlled vibration of the pin to separate the dispensed liquid material from the tip of the pin at a determined position.

In the aforesaid apparatus, the first actuator and/or second actuator may comprise a piezoelectric-stack. The pin may comprise an optical fiber. A light sensor can be coupled to the pin which can, during its operation, measure light intensity transmitted through the pin. The light intensity that is measured by the light sensor may provide an indication of the position of the pin in the bore.

A light sensor can be coupled to the pin. The sensor can comprise a beam splitter, a light source, and a first and second photodetector. During operation of light sensor, the first photodetector can detect light transmitted from the light source and reflected from the beam splitter and the second photodetector can detect light from the pin and reflected from the beam splitter. The apparatus also can include a means for indicating a position of the pin in the bore, the means is coupled to the pin. The apparatus also can include a means for indicating the amount of size of the dispensed liquid material.

In light of the above techniques, the following advantages are possible. The techniques can use a pin, such as light transmissive pin, to deliver predetermined amounts of liquid materials onto a surface by means of integrated sensing and control. An example of a light transmissive pin can include an optical fiber. The techniques can be used for such purposes as the preparation of nucleic acid microarrays, for microscopic markers, for micro-surgery or for pharmaceutical processing and drug discovery manipulations, or other purposes. This is accomplished without having the pin come into contact with the target surface, thus avoiding the high cost of replacing impact pins.

Moreover, the techniques may deliver precise metered liquids onto a surface with a controllable spot size. For example, using microstages to control the operation of the pin may allow the pin to be precisely position over the target surface. This may be accomplished at a low cost and with ease of operation. In addition, it may be possible to make efficient use of delivered liquids and avoid any waste of the liquid that is ejected from the reservoir. For example, the metered liquid sample adheres to the tip of the pin which is then delivered to the target surface. The use of a control system and position stages to control the operation of the liquid delivery apparatus may provide for a low cost, high yield, and flexible solution to the delivery of liquid onto a target surfaces.

Other features and advantages will be apparent from the following description, the accompanying drawings, and the claims.

BRIEF DESCRIPTION OF THE DRAWINGS

FIG. 4 is a table listing examples of light intensity values at different times during the operation of the liquid delivery system.

DETAILED DESCRIPTION

Figure 1:
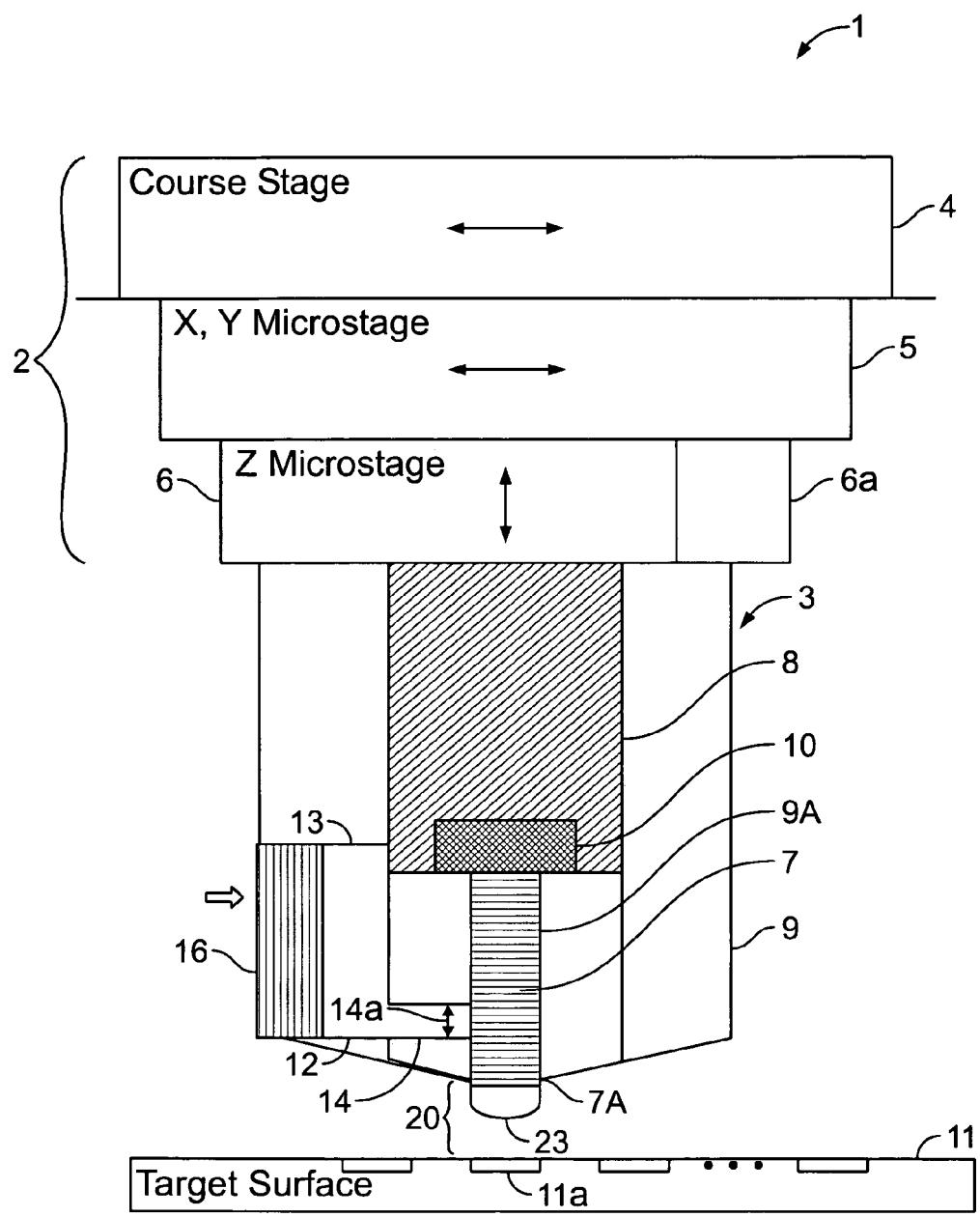
FIG. 1 is a cross-section diagram of an embodiment of a liquid delivery system.

FIG. 1 shows a liquid delivery system 1 that includes a positioning stage 2 coupled to a liquid delivery apparatus 3. The liquid delivery apparatus 3 uses a sensing and delivery pin 7 in combination with a sensor 10 to deliver a liquid sample 23 from a reservoir 12 to a target area 11a on a target surface 11. An example of a pin can include a light transmissive pin such as a fiber optic. In one embodiment, the liquid delivery apparatus 3 can deliver liquid materials including nucleic acids, proteins, polypeptides, or other materials to precise areas such as the target spots on a microarray. Liquid materials may include, for example, pure liquid compounds, mixtures, solutions, emulsions or dispersions. The liquid delivery apparatus 3 is capable of depositing liquid materials onto the preselected areas without coming into contact with the target surface 11.

The positioning stage 2 may include a coarse positioning stage 4 as well as a horizontal axis microstage 5 and a vertical axis microstage 6. Coarse positioning can be accomplished using robotic techniques having a wide range of motion. The microstages 5, 6 serve both to finely position the liquid delivery apparatus 3 and, in conjunction with vibration sensor 6A, to act as a vibration servomechanism to help remove vibration that may be caused by environmental and structural factors.

The horizontal microstage 5 provides fine positioning in the X, Y directions, whereas the vertical microstage 6 provides fine positioning in the Z direction. The microstages can be implemented, for example, using piezoelectric, magnetostrictive or shape memory materials that can physically deform in a precise manner in response to electrical signals. In one particular implementation, the microstages can be implemented using a piezoelectric actuator capable of providing up to six degrees of positioning freedom as disclosed in U.S. Pat. No. 6,359,370, Chang. The actuator is capable of providing positioning freedom in the/linear directions (X, Y, Z) and three rotary angles.

The vibration sensor 6A can include, for example, one or more linear accelerometers coupled to the vertical microstage 6 to provide vibration control. Vibration control is important for precisely locating the delivery point a few microns above the target surface 11. Vibration control can be achieved by use of a separate vibration-controlled table on which the delivery apparatus is mounted. Alternatively, vibration control can be included in the delivery apparatus itself. Known techniques may be used to provide vibration control. For example, point vibration suppression can be realized by using a piezoelectric actuator located between a robotic platform and the load, in this case the pin 7. See, e.g. Chang, T. N. and Davison, E. J., "Decentralized Controller Design Using Parameter Optimization Method," C-TAT, vol. 2, No. 288, pages 131–154 (1986); and Chang, T. N. et al., "Vibration Control of Linear Robots Using Piezoelectric Actuators," Proceedings of the 2000 American Control Conference, Chicago, Ill., June 28–30, pp. 2523–2527.

As shown in FIG. 1, the pin 7 is disposed in a housing 9 and is vertically translatable in a cylindrical bore 9A of the housing. The pin 7 is used for sensing the distance of its tip above the surface and for delivering a drop of liquid to the surface; that is, it is a sensing and delivery pin. The housing can be formed of any suitable material such as plastic or silicon. In one implementation, the pin 7 includes a fiber optic having a diameter in the range of 5 to 50 microns. The fiber optic tube can be formed from inexpensive materials such as plastic or from more expensive materials such as silicon or metal. The diameter of the fiber optic pin may be based on factors such as the size of liquid material to be dispensed, the electrical characteristics of the light sensor, or other factors. The pin 7 is driven vertically by a pin actuator 8 which may include piezoelectric, magnetostrictive or shape memory materials, and which responds to electrical signals.

The light sensor 10 is coupled to the top portion of the pin 7 and is used to sense the light reflected from the target surface 11 and transmitted through the bottom surface of the pin 7. The bottom portion of the pin 7 closest to the target surface 11 can be polished to form a lens which can improve the light focusing ability of the pin. The light sensor 10 is described in further detail below.

The liquid material reservoir 12 includes a port 13 through which a liquid material may be added and a delivery port 14 that is coupled to the cylindrical bore 9A. A reservoir actuator 16, which may include a piezoelectric pump, delivers a metered amount of liquid material from the reservoir 12 into the cylindrical bore 9A through the delivery port 14. The delivery port 14 has an orifice 14a with a diameter whose sized may be based on factors such as the metered amount of liquid material that is to be dispensed. The diameter of the orifice 14a can range, for example, from 5 to 20 microns.

The pin driver 8 may include a piezoelectric linear actuator, such as an electronically controlled piezoelectric stack. When the tip 7A of the pin 7 is correctly positioned above the target surface 11, a high-frequency vibration from the piezoelectric actuator causes the liquid material droplet 23 to separate from the tip 7A and to be deposited on the target area 11a of the target surface 11. For example, the piezoelectric actuator can be physically displaced approximately 10 microns at one of its resonant frequencies in the kHz range. Extremely small droplets can be delivered at high speed. For example, a fiber optic pin 7 having a diameter of 50 microns can deliver droplets as small as 0.1 picoliter.

Vibration of the pin can be carried out in two different ways: force oscillation or sustained resonance by means, for example, of an automatic gain control (AGC) loop. The force oscillation method entails the injection of a periodic signal to the pin driver 8 so as to generate a rapid vibration in the Z direction. The second, and preferred, approach is to induce oscillation at the pin driver's 8 resonant frequency, which is usually in the tens of kHz range. The AGC loop can be tuned to achieve regulated amplitude while minimizing the drive voltage into the pin driver. Details of the AGC loop construction is taught in (Chang, T. N., Ljung, B., and Friedland, B.), "System for Substantially Eliminating Lock-in in a Ring Laser Gyroscope," U.S. Pat. No. 5,359,413.

Figure 2A:
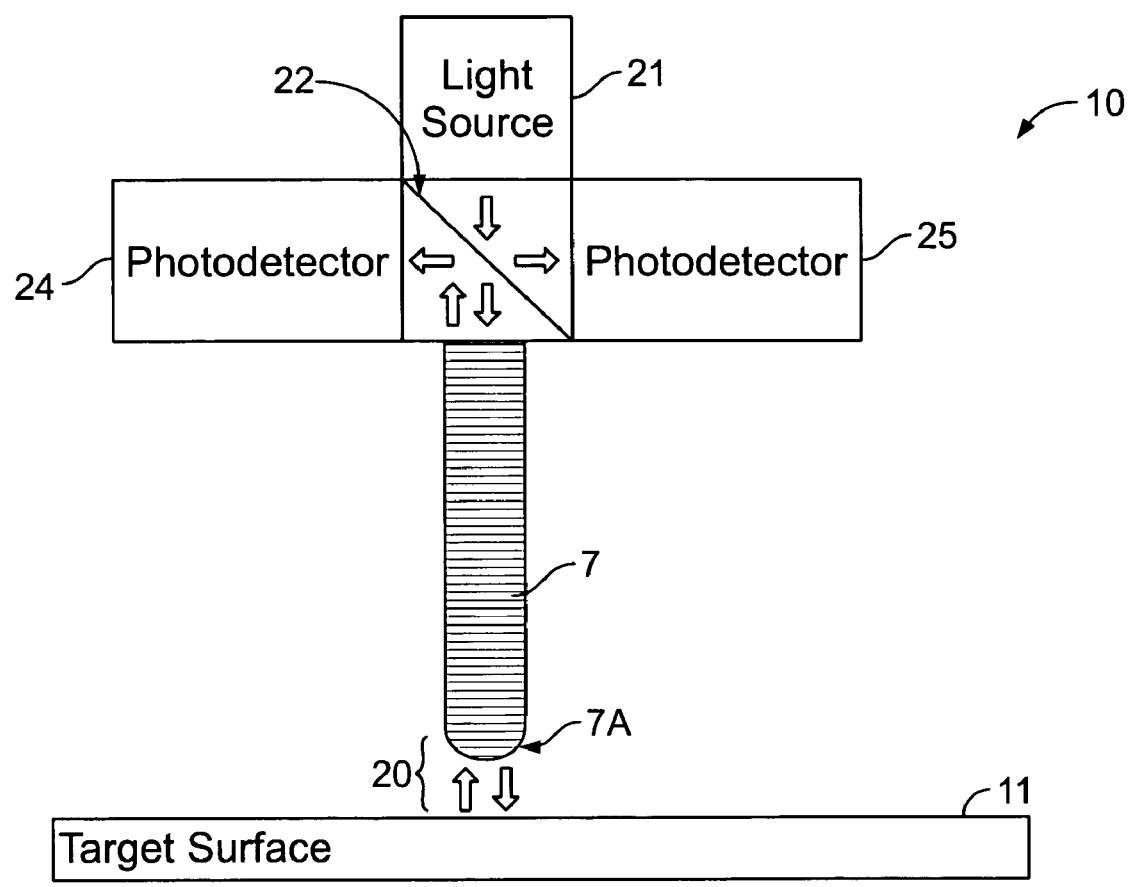
FIGS. 2A–2B illustrate embodiments of a light sensor in the liquid delivery system.
Figure 2B:
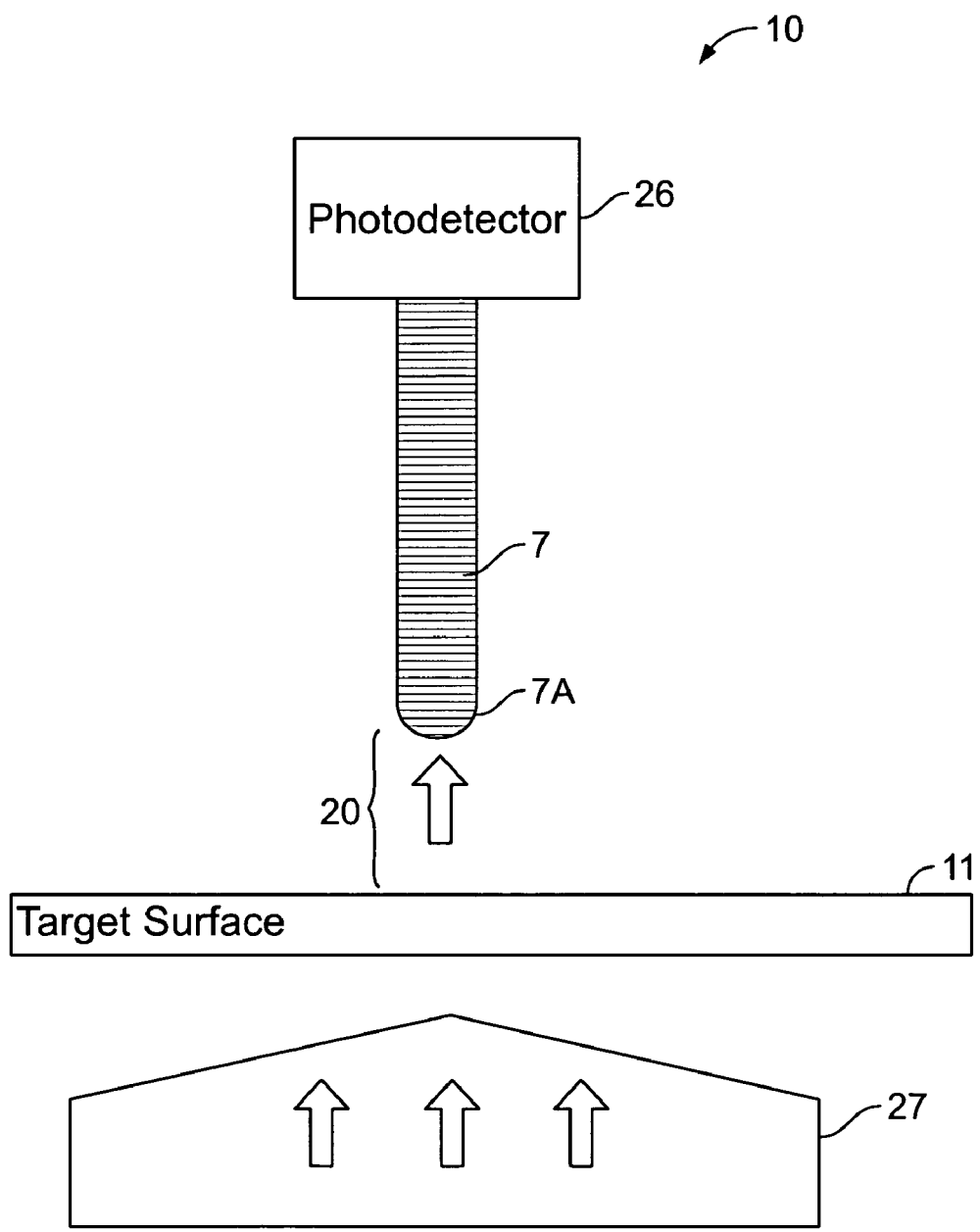

FIGS. 2A–2B show different embodiments of the light sensor 10 used in the liquid delivery apparatus 3. Optical transmission through the pin 7 may be either two-way, which we refer to as the "active" mode, or one-way, which we refer to as the "semi-active" mode. FIG. 2A shows the "active" mode in which the light sensor 10 is mounted to the top of the pin 7 and is vertically translatable with the pin. The light sensor 10 includes a light source 21, a beam splitter 22, and photodetectors 24, 25. The light source 21 can be any suitable source of monochromatic or polychromatic light, for example, a laser or a light emitting diode (LED). The splitter 22 sends a portion of the light from light source 21 to photodetector 25 which monitors the intensity of the source. The splitter 22 sends a portion of the light from the light source 21 down through the pin 7 and onto the target surface 11. The splitter 22 sends reflected light passing back up through the pin 7 to photodetector 24, which monitors the intensity of the reflected light. The distance 20 between tip 7A of the pin 7 and target surface 11 can be determined based on the reflected light. In some implementations, that distance may be determined to within approximately 0.1 micron.

In the "semi-active" mode as shown in FIG. 2B, the light sensor 10 includes a photodetector 26 mounted to the top of the pin 7. A light source 27 provides a light beam from below the target surface 11 which can be semi-transparent or transparent. The photodetector 27 measures the intensity of the light that travels from the target surface 11 and through the pin 7. The distance 20 between the tip 7A and the target surface 11 may be determined based on the detected light.

In both the active and the semi-active modes, light is transmitted from the target surface 11 through the pin 7 which acts as an optical transmission line. The light that travels through the optical transmission line is sensitive to different refractive indices of air, the fiber, the nature of the liquid sample 23, the shape of the material in its path, or other factors. As a result, near-contact condition of the pin and the target surface can be derived by continuously or intermittently monitoring the light intensity at the photodetector(s).

Although optical sensing 10 can be used to provide an indication of the position of the pin 7 as it travels in the bore 9A, other sensing techniques can be used. For example, capacitive or inductive sensing techniques can be used along with corresponding sensing means.

Figure 3:
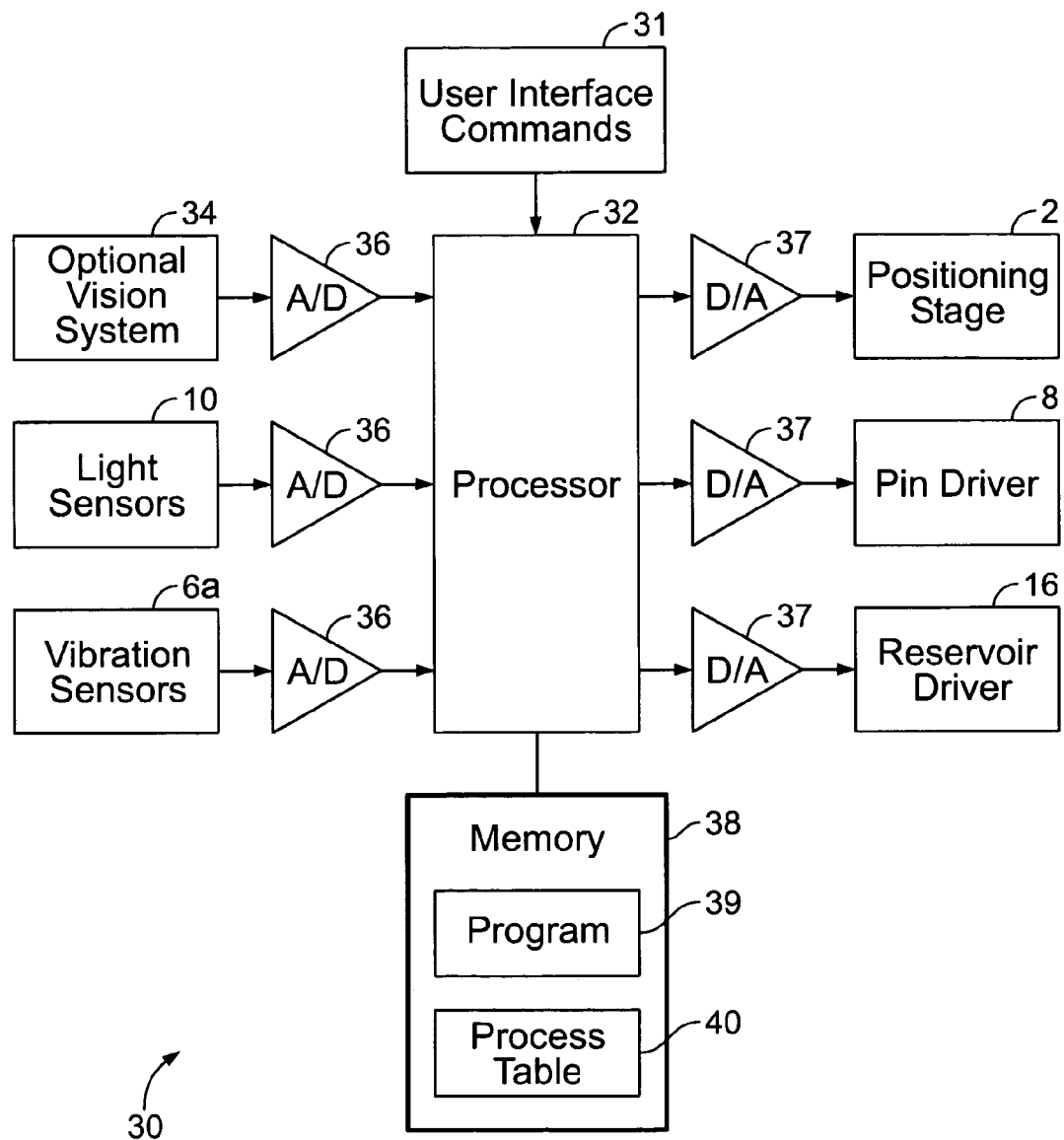
FIG. 3 is a block diagram of a control system for the liquid delivery system.

FIG. 3 shows a block diagram of a control system 30 for controlling the operation of the liquid delivery system 1. The control system 30 may utilize feedforward/feedback control and advanced signal processing to minimize hardware cost. The control system 30 includes a processor 32, such as a digital signal processor (DSP), and a memory 38 to store a software program 39 and a process table 40. The processor 32 executes the program 39 which includes software instructions to control the overall operation of the system 1 including the liquid delivery apparatus 3.

The process table 40 includes light intensity data corresponding to different time intervals which the processor 32 can use during a process cycle to determine the position of the pin 7. In a typical process cycle, the pin 7 is positioned at the top-most portion of the bore 9A, the pin is moved downward toward the target area 11a of the target surface 11 causing the liquid sample 23 to adhere to the tip 7A of the pin 7, and then the liquid sample is separated from the tip 7A of the pin 7 and onto the target area 11a when the pin reaches a predetermined distance 20 above the target surface. (see FIG. 1) The processor 32 may create the process table 40 during a test process cycle and can use the table during an actual production process cycle. The creation and use of the process table 40 are described in further detail below.

A user interface 31 allows a user or another program to enter commands to control the factors involved in the process cycle. Those factors may include the number of droplets to deposit on a particular target surface (i.e. slide), the amount of the deposit, the number of slides or other factors. The user interface 31 can allow commands to be entered locally through a computer terminal coupled to the control system or remotely over a network.

The processor 32 controls the operation of the various components of the system by executing the program 39 during a process cycle. The program 39 can include software instructions for generating digital signals which are translated into analog signals by digital-to-analog (D/A) converters 37. The processor 32 can send signals to the positioning stage 2 including the coarse stage 4, the horizontal microstage 5, and the vertical microstage 6 to move the liquid delivery apparatus 3 to the appropriate target area 11a over the target surface 11. Likewise, the processor 32 can send signals to the pin driver 8 to control the vertical translation motion of the pin 7 within the bore 9A. In a similar manner, the processor 32 can send signals to the reservoir actuator 16 to control the amount of liquid sample 23 that is ejected into the bore 9A and subsequently attached to the tip 7A of the pin 7. The pin driver 8 also can respond to high frequency signals from the processor 32 to cause the liquid sample 23 to separate from the tip 7A of the pin 7 and fall onto the target surface 11.

Analog-to-digital (A/D) converters 36 may be used to translate analog signals generated by the sensor components of the system into digital signals which the processor can use to monitor execution of the process cycle. For example, analog signals from the vibration sensors 6A that indicate the amount of vibration occurring in the system 1 can be converted into digital signals. Similarly, A/D converters 36 can convert analog signals from the light sensor 10 into digital signals. These signals provide an indication of the intensity of light transmitted through pin 7 such that the position of the pin can be inferred. The optional vision system 34 may include one or more video cameras positioned on or around the target surface 11 and/or the liquid delivery apparatus 3. The system 34 can provide video signals which are converted into digital signals by the A/D converters 36. The system 34 can allow users to monitor the operation of the liquid delivery system 1 from a remote location including the same facility where the apparatus 3 is located or monitored from a remote location over a network such as the Internet.

The A/D converters 36 and the D/A convertors 37 can be implemented, for example, using 12-bit converters having an output voltage range of approximately −5 to 5 volts which corresponds to a step size of approximately of 2.5 millivolts. The sampling rate of the converters 36, 37 can be adjusted according to the accuracy desired. For example, the sampling rate can be set to approximately 100 microseconds to provide adequate output resolution and accuracy.

FIG. 4 shows an embodiment of the process table 40 that includes one or more light intensity entries 42 representing the amount of light received at the light sensor 10 during different time periods represented by one or more time entries 41 during the execution of a process cycle.

The time entries 41 include time values representing intervals of time in time units, such as microseconds, that have elapsed since the beginning of a process cycle. The light intensity entries 42 include data values in magnitude units, such as volts, representing the light intensity received from the light sensor 10 at each of the time intervals during the process cycle. As mentioned above, the light sensor 10 serves as an optical transmission line and allows near-contact condition to be derived by continuously or intermittently measuring the light intensity values at the light sensor 10.

The processor 32 may generate the entries in the process table 40 by executing one or more test process cycles. A statistical function, such as an average function, may be applied to the data produced during the test process cycles to derive values for the table. The processor 32 retrieves the entries from the table 40 during an actual production process cycle to control the motion of the pin 7 and the delivery of the liquid sample 23 onto the target surface 11.

Figure 5:
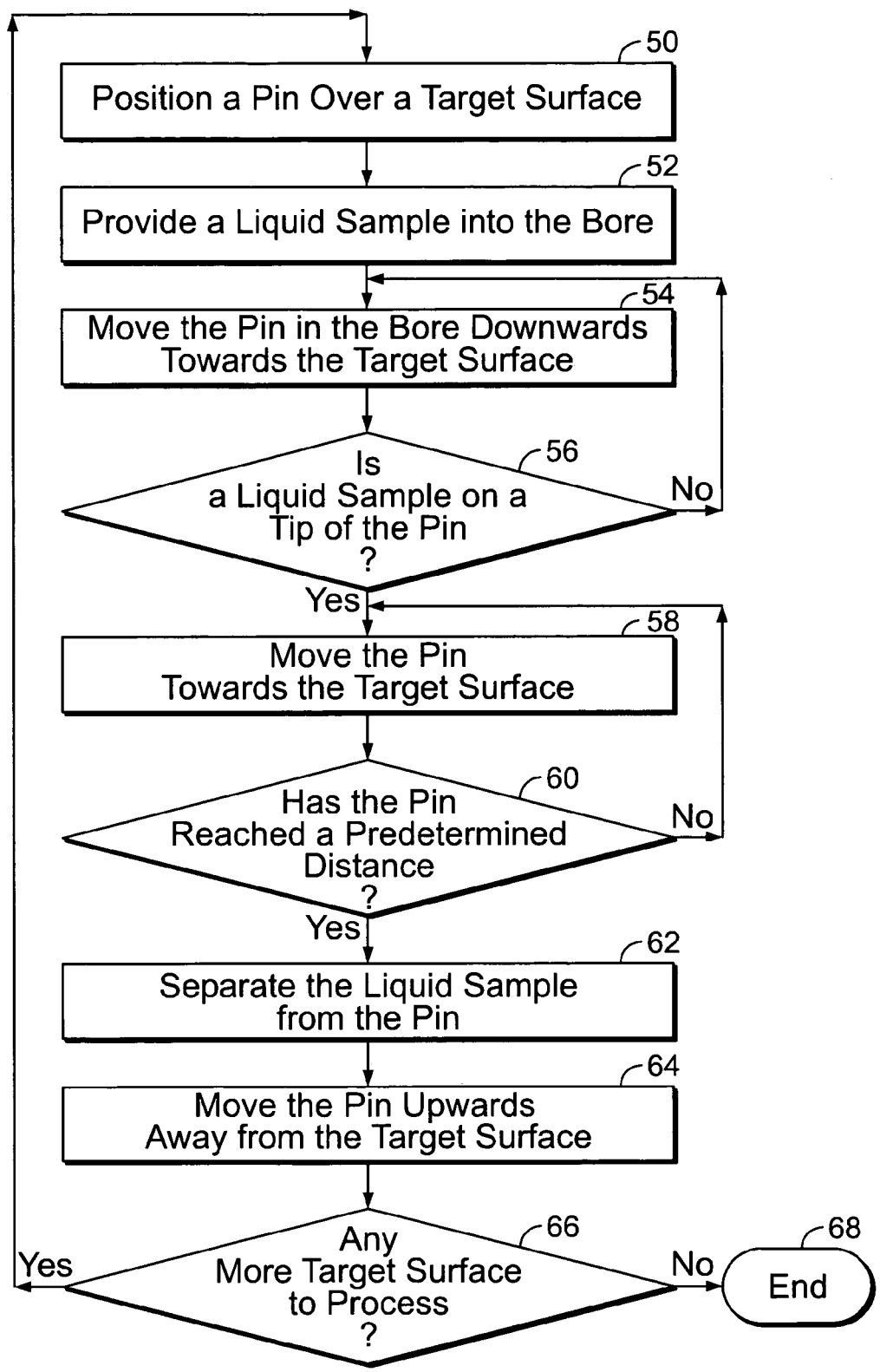
FIG. 5 is a flow diagram of the operation of the liquid delivery system.
Figure 6A:
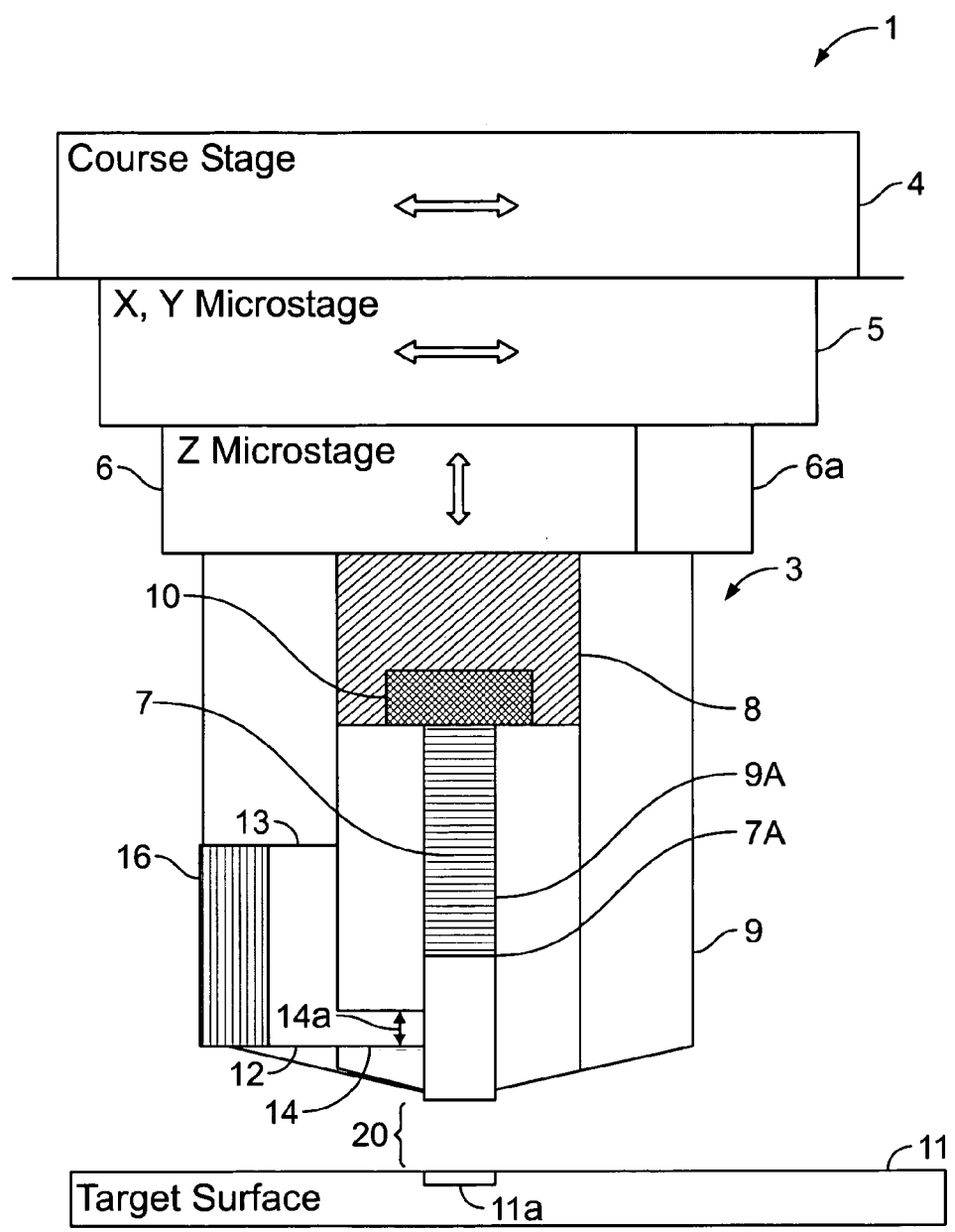
FIGS. 6A–6G illustrate the operation of an embodiment of a liquid delivery system during different stages of operation.

FIG. 5 is a flow diagram illustrating the operation of the liquid delivery system 1. As mentioned above, the processor 32 executes the program 39 for controlling the operation of the liquid delivery system 1 during a process cycle. The pin 7 of the apparatus 3 is positioned (block 50) over a target surface 11 in preparation for the process cycle that includes depositing a liquid sample on a target area 11a of the target surface. (See FIG. 6A) This can be accomplished by having the processor 32 send signals to the coarse stage 4, the horizontal microstage 5, and the vertical microstage 6 to move the apparatus 3 to the appropriate spot over the target surface 11.

Figure 6B:
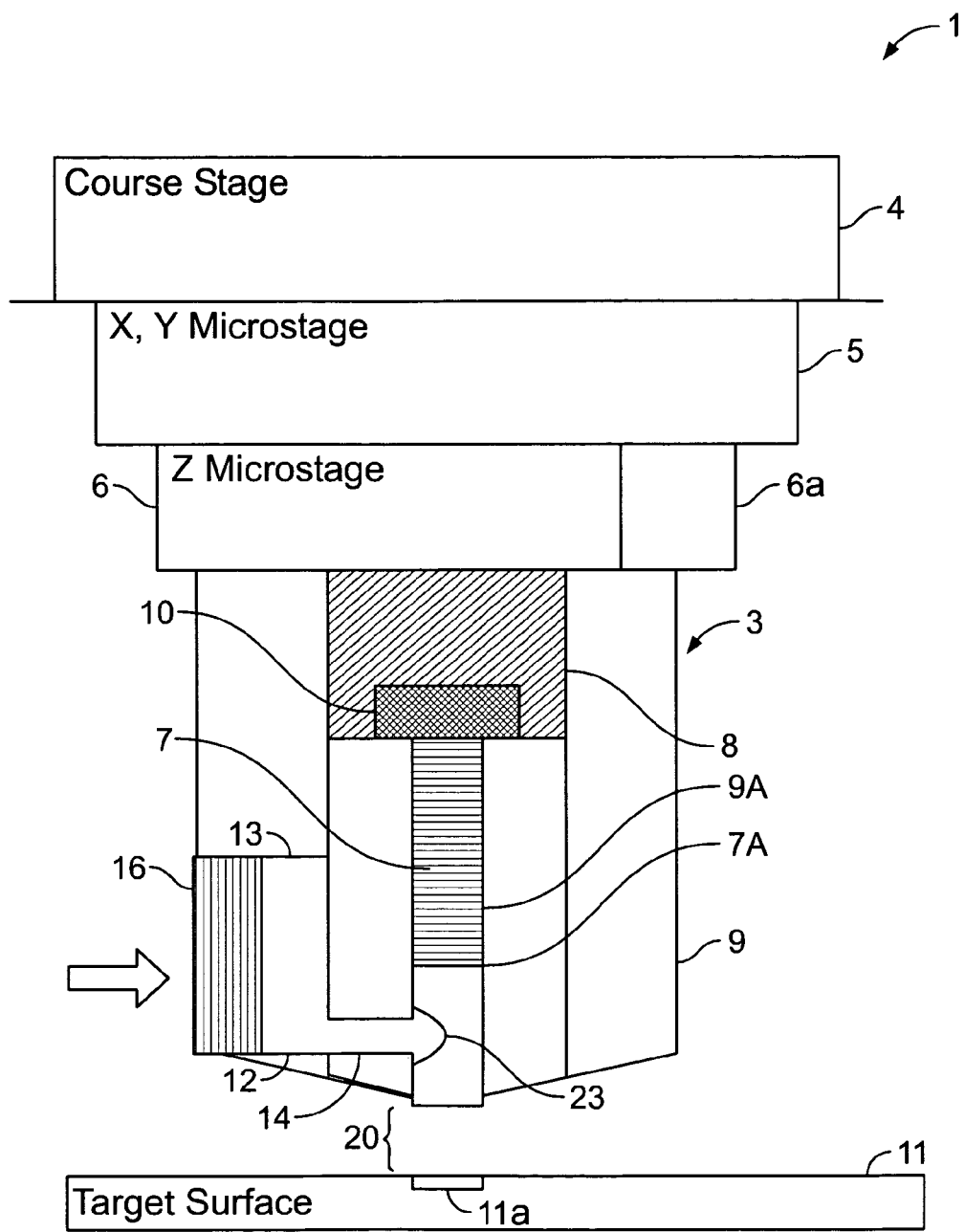
Figure 6C:
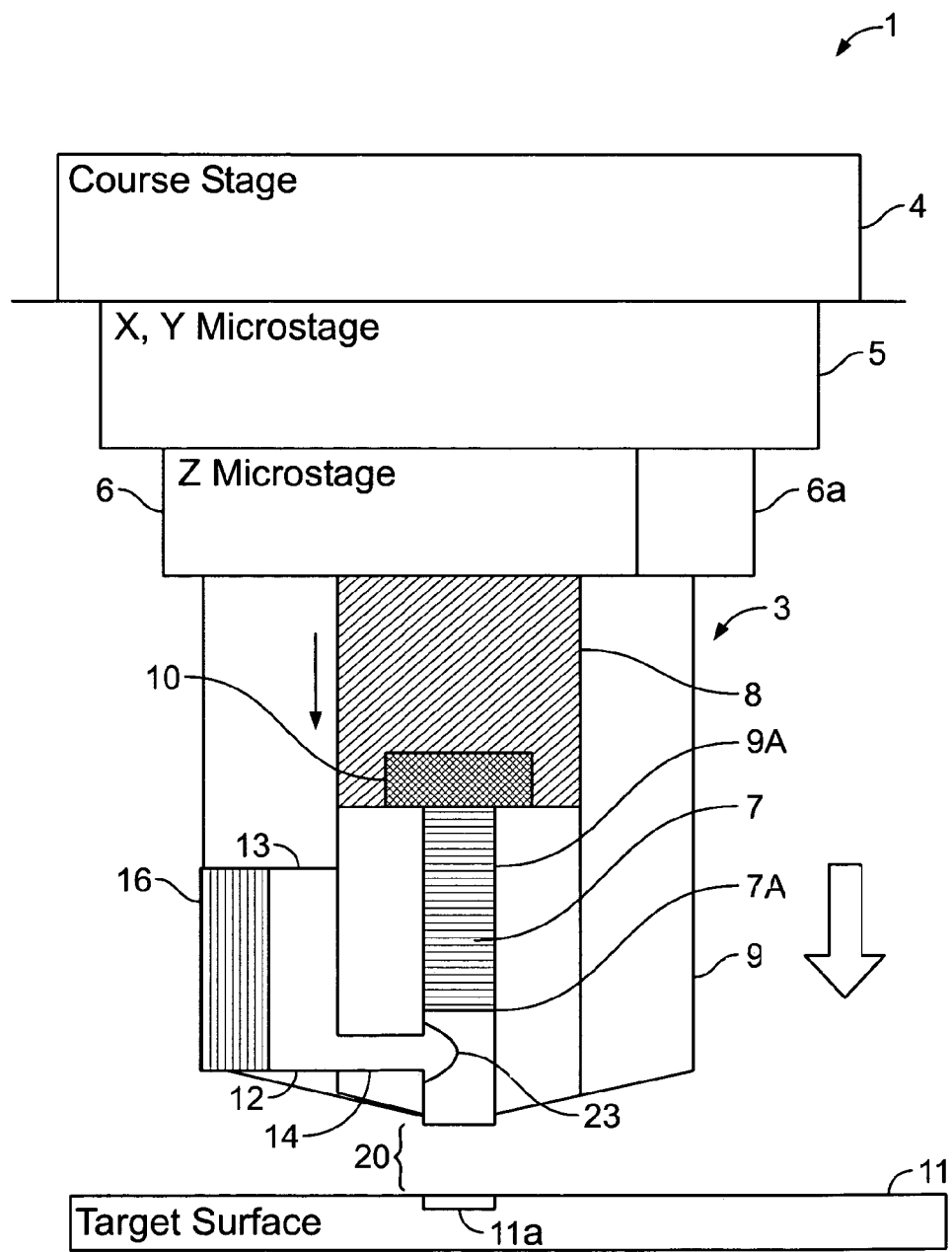

Once the liquid delivery apparatus 3 is positioned over the target surface 11, the processor 32 causes 52 a predetermined liquid sample 23 to be provided at the interface of the orifice 14 and the bore 9A. (See FIG. 6B) The liquid sample 23 remains at the interface as a result of forces such as surface tension. This can be accomplished by having the processor 32 send signals to the reservoir actuator 16 to cause a predetermined amount liquid sample to be ejected from the reservoir 12. At or around the same time, the pin 7 is moved 54 in the downward direction toward the target surface 11 as a result of signals from the processor 32 to the pin driver 8. (See FIG. 6C)

Figure 6D:
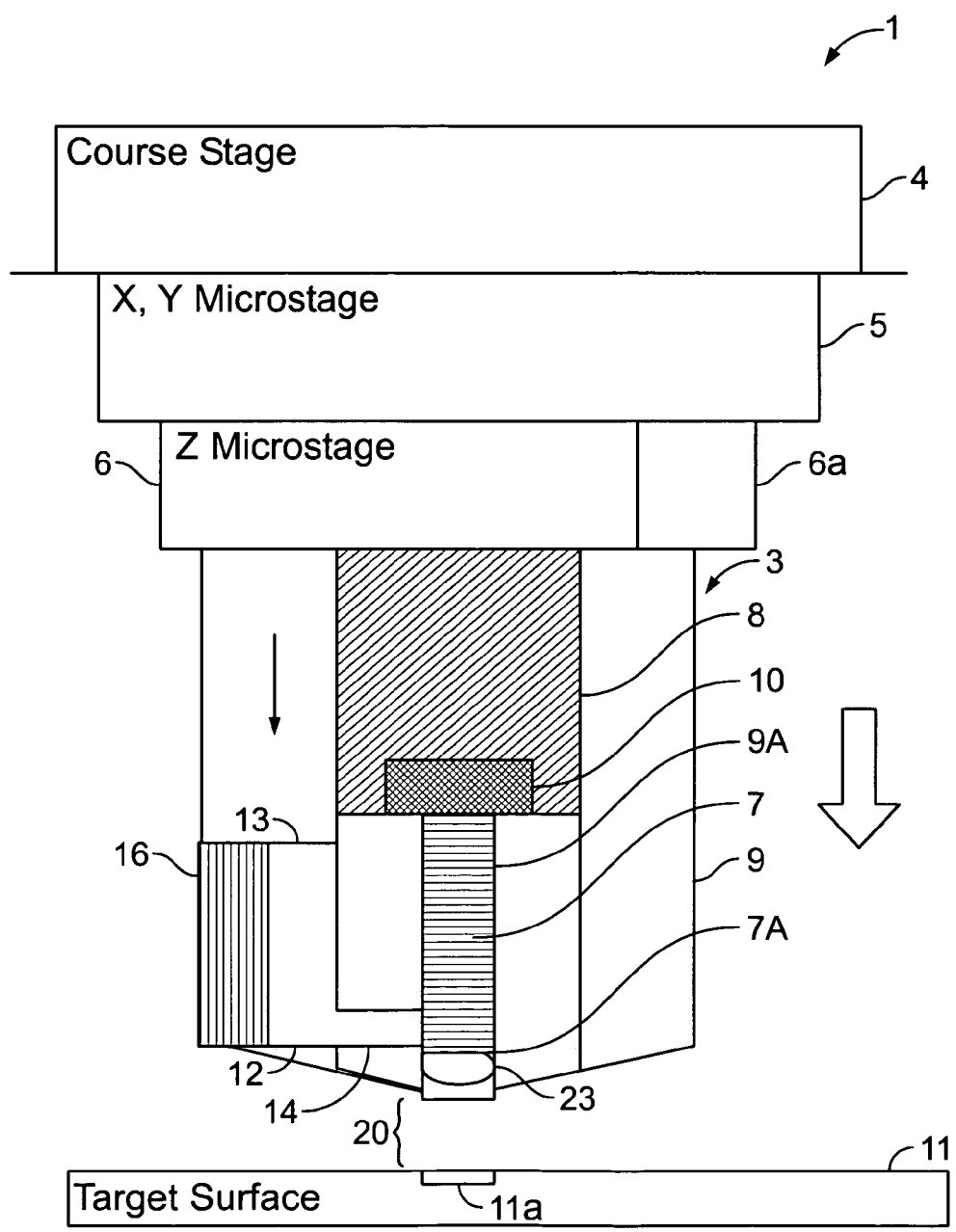

As the pin 7 travels downward in the bore 9A toward the target surface 11, the processor 32 determines 56 whether the liquid sample 23 in the bore 9A is adhered to the tip 7A of the pin 7. (See FIG. 6D) The liquid sample 23 remains on the surface of the tip 7A of the pin 7 as a result of forces such as capillary action. The processor 32 can monitor and receive light intensity signals from the light sensor 10 as light is transmitted through the pin 7.

In one embodiment, the processor 32 retrieves from the process table 40 a light intensity entry 42 that corresponds to the current time as represented by the time entry 41. (See FIG. 4) For example, at the beginning of the process cycle, the time entry 41a has a time value of 0 milliseconds (msec) and a corresponding light intensity value 41b has a value of 0 volts. As the process cycle proceeds, the intensity of the light signal increases, for example, at 1 msec from the beginning of the process cycle, the processor 32 retrieves the light intensity entry 42b which has a value of 0.5 volts representing the approximate light intensity that is expected at this time. This expected light intensity is compared with the received light intensity to determine whether there is a substantial match between the intensity values indicating that the liquid sample 23 is attached to the pin 7. If there is no match, the process returns to block 54 where the pin 7 is moved further downward in the bore 9A toward the target surface 11 until the liquid sample 23 is attached to the tip 7A of the pin 7 and there is a substantial match between the received and the expected light intensity values.

Once the processor 32 determines that the liquid sample 23 is attached to the tip 7A of the pin 7, the pin is moved 58 further downward towards the target surface 11. For example, referring to FIG. 4, if the current time is 5 msec from the beginning of the process cycle, the processor 32 retrieves the light intensity entry 42c which has a value of 5 volts representing the light intensity that is expected at this time. As the pin 7 moves downward past the delivery port, it not only obtains the liquid sample 23, but it also blocks and prevents any more samples from leaking into the bore 9A.

Figure 6E:
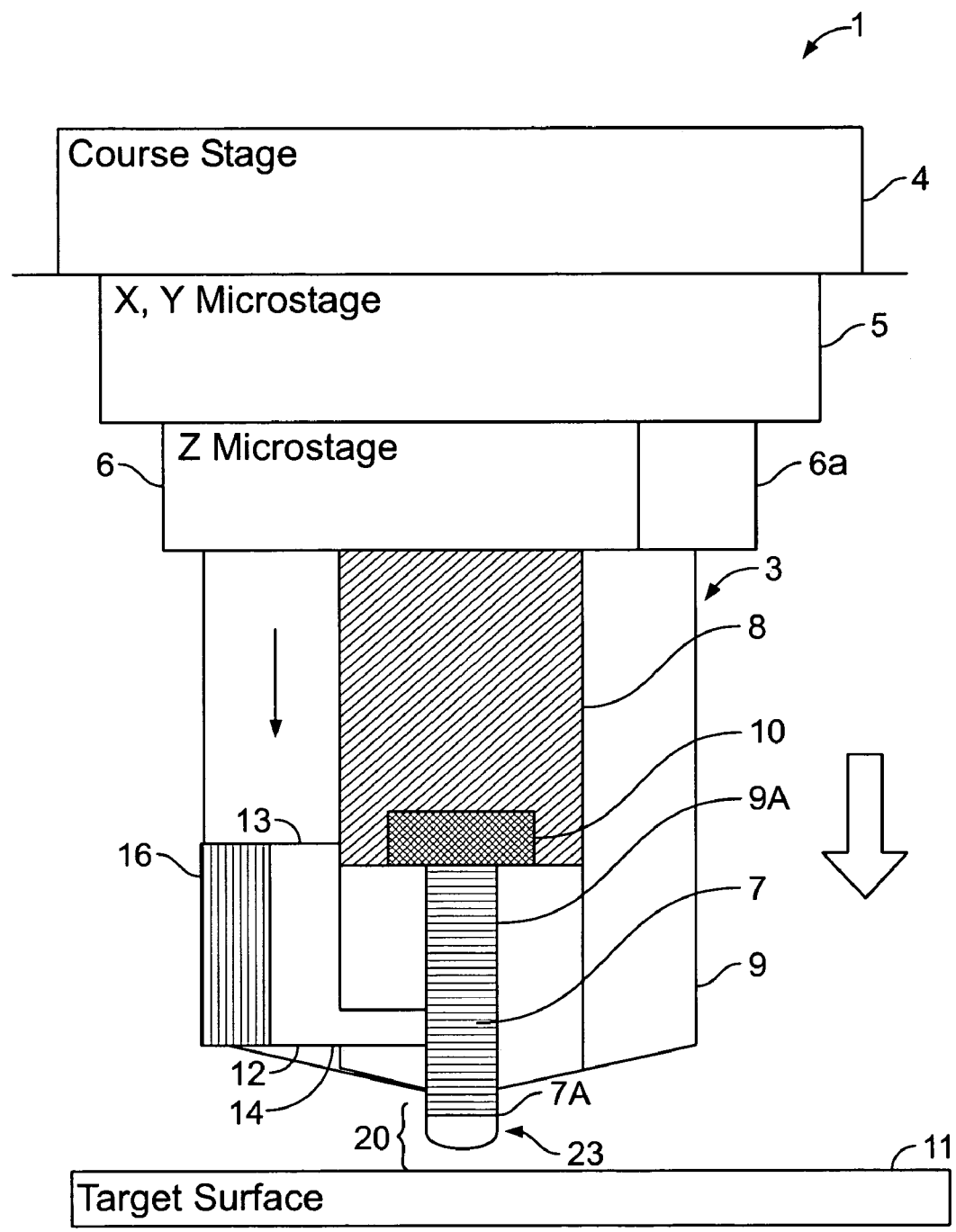

As the pin 7 travels downward in the bore 9A, the processor 32 determines 60 whether the pin has reached a predetermined distance 20 from the target surface 11. (See FIG. 6E) As explained above, the processor 32 monitors and receives signals from the light sensor indicating the intensity of light transmitted through the pin 7. For example, referring to FIG. 4, if the current time is 6 msec from the beginning of the process cycle, then the processor 32 retrieves the light intensity entry 42d which has a value of 4.0 volts representing the light intensity that is expected at this time. This expected value represents the light intensity as a result of the liquid sample attached to the tip 7A of the pin 7 and being at a predetermined distance 20 from the surface. This expected light intensity can then be compared with the received light intensity to determine whether there is a match indicating that the pin 7 has reached a predetermined distance 20 from the target surface 11. If there is no match, the process returns to block 58 where the pin 7 is moved further in the bore 9A in the downward direction towards the target surface 11 until the pin reaches the predetermined distance 20.

Figure 6F:
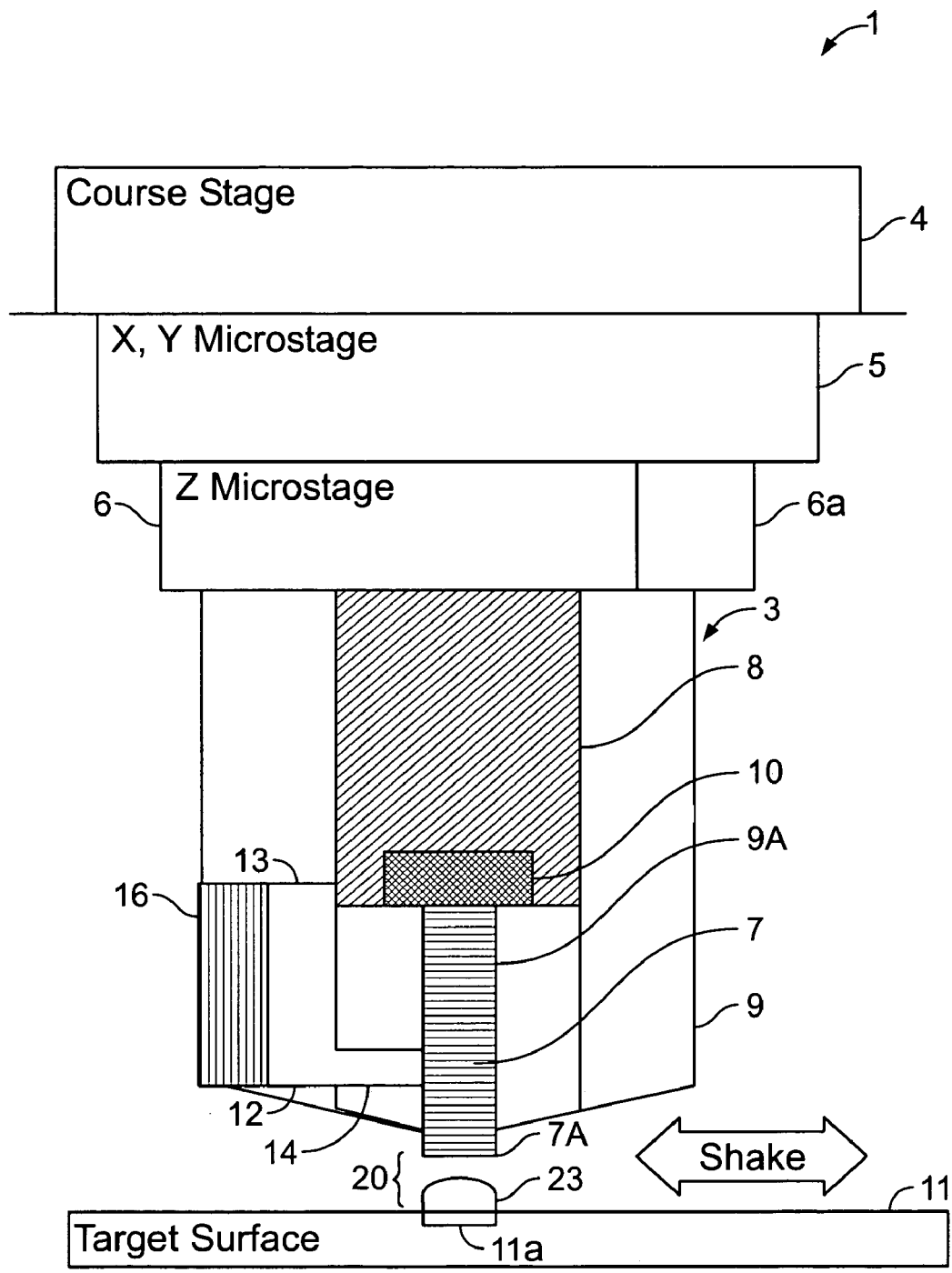

Once the pin 7 has reached the predetermined distance 20, the processor 32 causes the liquid sample 23 to separate 62 from the tip 7A of the pin 7 and fall onto the target area 11a. (See FIG. 6F) The processor 32 sends high frequency signals to the pin driver 8 which causes the pin 7 to vibrate in a controlled manner resulting in the liquid sample 23 separating from the tip 7A of the pin 7. Furthermore, the target surface 11 may be coated with a hydrophilic material which binds the droplet to the surface as soon as the droplet comes into contact with the surface. As a result, the pin 7 is able to deposit a liquid sample 23 onto the target surface 11 without having the tip 7A of the pin 7 makes contact with that surface. The light intensity measured by the light sensor can provide an indication of the size of the dispensed liquid material and hence the presence/absence of the droplet can be detected. For example, when a droplet contacts the target slide, an abrupt transition may occurs which may cause the voltage to change accordingly. The larger the droplet, the larger the dispersive effect and hence a larger drop in intensity.

Figure 6G:
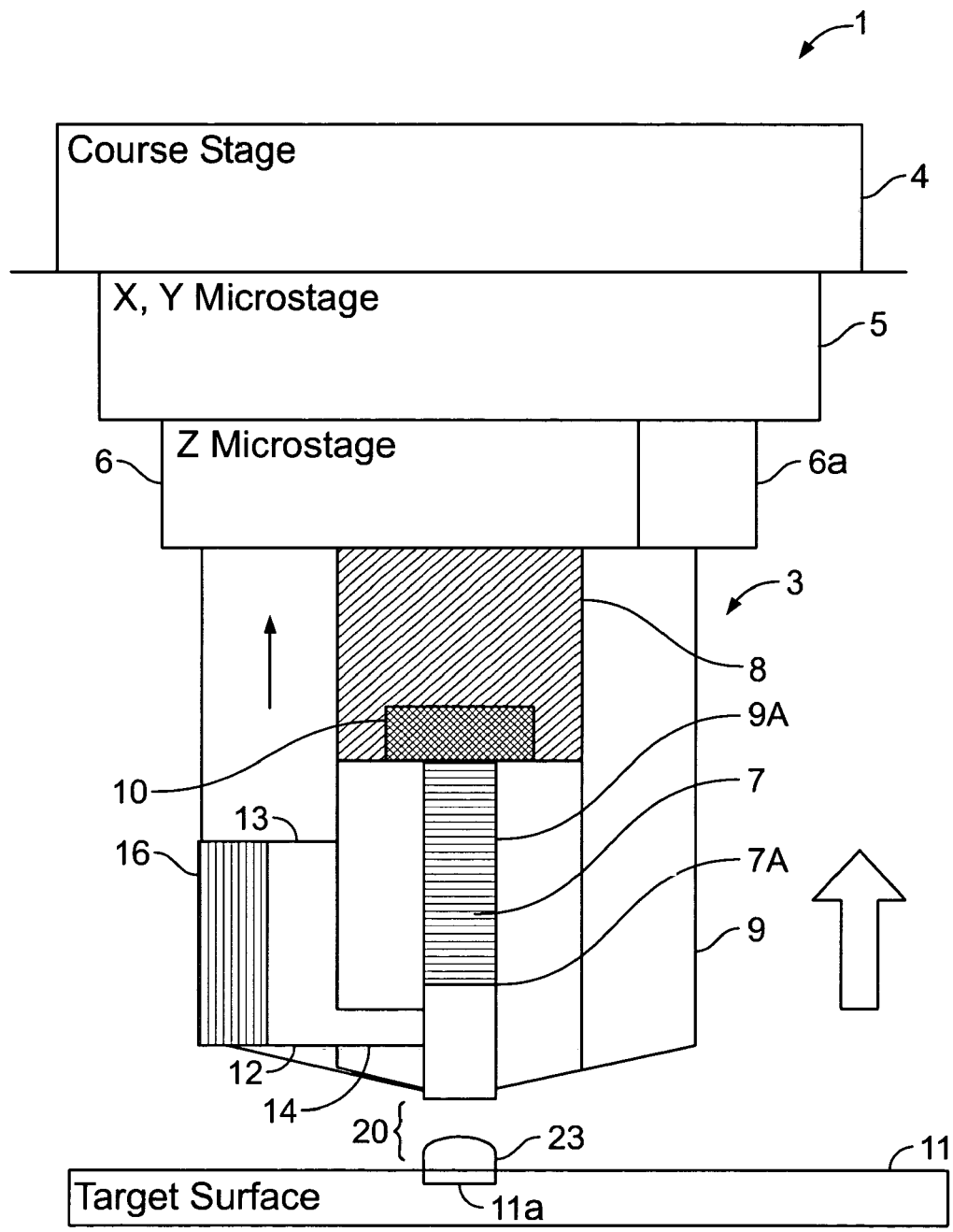

The processor 32 retrieves a light intensity entry from the process table 40 to determine whether it is time to cause the pin 7 to move in an upward motion away from the target surface 11. For example, if the current time were 7 msec from the beginning of the process cycle, the processor 32 would retrieve the light intensity entry 42e which has a value of approximately 2.5 volts indicating the expected light intensity value at this time in the process cycle. This expected light intensity value represents the condition in the process cycle when the liquid sample has separated from the tip 7A of the pin 7. This expected light intensity is compared with the received light intensity to determine whether the liquid sample 23 been separated from the pin 7. Once the liquid sample has been deposited onto the target surface 11, the processor 32 sends signals to the pin driver 8 to cause the pin 7 to move 64 in the upward direction away from the target surface 11. (See FIG. 6G).

As the pin 7 is being moved in the upward direction away from the target surface 11, the processor 32 checks 66 whether the process cycle for depositing liquid samples on each of the target areas 11a on the target surface 11 is complete. If each of the target areas 11a has been processed, the process cycle for a target surface 11 is complete and the processed target surface can be removed and replaced with a new target surface for the next process cycle. On the other hand, if there remain unprocessed target areas 11a on the target surface 11 that have not received a liquid sample, the process returns to block 50 where the pin 7 is moved to the next unprocessed target area 11a on the target surface 11.

Figure 7A:
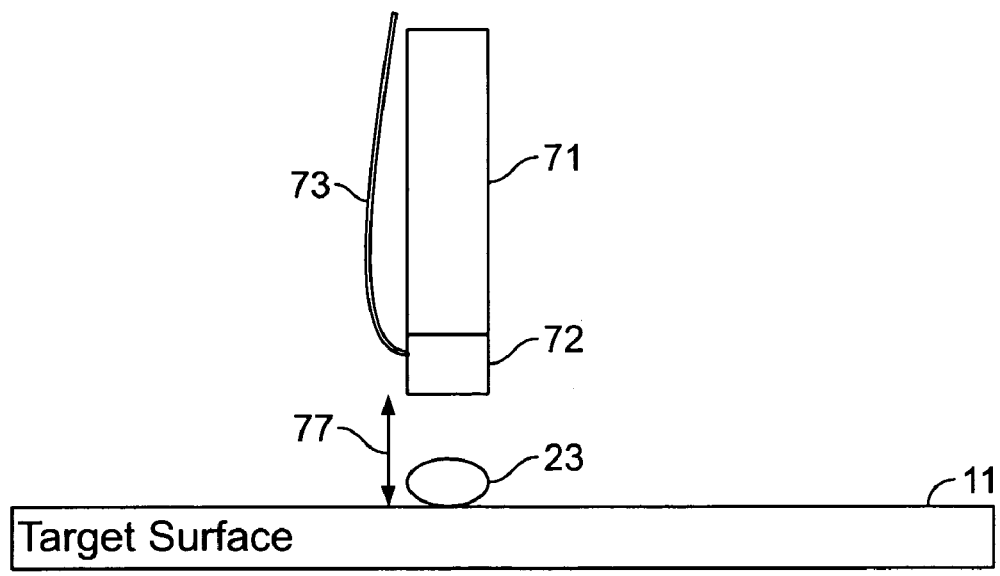
FIGS. 7A–7B illustrate embodiments of the pin.

Although the pin discussed above was in the context of a light transmissvie pin, other implementations of the pin are possible. For example, FIG. 7A shows a mechanical pin 71 with a small photodetector 72 mounted at the tip of the pin. The mechanical pin 71 serves as the plunger to deliver the liquid sample 23 while the photo detector 72 monitors the liquid formation and target distance 77. Electrical wirings 73 may be required to bring signals from the photodetector 72 to the controller(not shown).

Figure 7B:
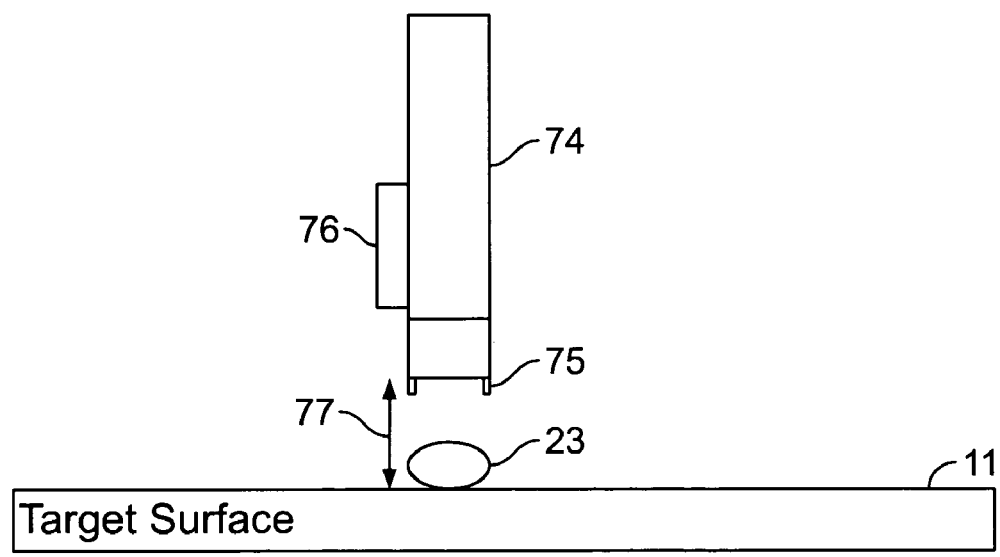

FIG. 7B shows another implementation of the pin in which non-optical means of sensing can be used such as, for example, electrical/magnetic means. In one implementation, the pin 74 can include a pair of electrodes 75 mounted to the tip of the pin. The pair of electrodes 75 can detect the contact resistance to monitor the liquid formation (with out liquid, the electrodes constitute an open circuit, otherwise, the resistance particular to the sample material can be measured to determine parameters related to the liquid such as spot size). Additional sensors 76 (capacitive/inductive) can be mounted to the pin 74 to measure the target distance 77.

Other implementations are within the scope of the following claims.

What is claimed is:

1. A liquid delivery apparatus comprising:
a housing including a bore;
a pin including a tip, the pin movably disposed within the bore;
a reservoir including a port with an opening adjacent a side of the bore, the reservoir for holding a liquid material for delivery to the opening;
a first actuator coupled to the reservoir to dispense a metered amount of the liquid material from the reservoir to the opening; and
a second actuator coupled to the pin providing controlled movement of the pin within the bore, including movement of the tip past the opening to adhere dispensed liquid material to the tip, the second actuator also providing controlled vibration of the pin to separate the adhered liquid material from the tip of the pin at a determined position.

2. The apparatus of claim 1 wherein the first actuator comprises a piezoelectric-stack.

3. The apparatus of claim 1 wherein the second actuator comprises a piezoelectric-stack.

4. The apparatus of claim 1 wherein the pin comprises an optical fiber.

5. The apparatus of claim 1 further comprising a light sensor coupled to the pin for measuring the intensity of light transmitted through the pin.

6. The apparatus of claim 5 wherein the light intensity measured by the light sensor provides an indication of the position of the pin in the bore.

7. The apparatus of claim 5 wherein the light intensity measured by the light sensor provides an indication of the size of the dispensed liquid material.

8. The apparatus of claim 1 further comprising a light sensor coupled to the pin, wherein the light sensor comprises a beam splitter, a light source, a first photodetector, for detecting light transmitted from the light source and reflected from the beam splitter and the second photodetector detects light from the pin and reflected from the beam splitter.

9. The apparatus of claim 1 further comprising a means for indicating a position of the pin in the bore, the means coupled to the pin.

10. The apparatus of claim 1 further comprising a means for indicating the size of the dispensed liquid material, the means coupled to the pin.

11. A liquid dispensing system comprising:
a positioning stage; and
a liquid delivery apparatus coupled to the positioning stage to move the liquid delivery apparatus, the liquid delivery apparatus comprising:
a housing including a bore and a liquid delivery port having an orifice opening into a side of the bore,
a pin including a tip, the pin movably disposed within the bore,
a reservoir for holding a liquid material for delivery to the delivery port,
a first actuator coupled to the reservoir to dispense a metered amount of the liquid material from the reservoir to the interface of the orifice and the bore, and
a second actuator coupled to the pin providing controlled movement of the pin within the bore, including movement of the tip past the orifice to adhere dispensed liquid material to the tip, the second actuator also providing controlled vibration of the pin to separate the dispensed liquid material from the tip of the pin at a determined position.

12. The system of claim 11 wherein the positioning stage comprises a coarse positioning stage and a fine positioning stage.

13. The system of claim 12 wherein the coarse positioning stage comprises a robotic device.

14. The system of claim 12 wherein the fine positioning stage comprises a horizontal microstage and a vertical microstage.

15. The system of claim 14 wherein each microstage comprises a piezoelectric-stack.

16. The system of claim 14 wherein the fine positioning stages further comprises a vibration control stage.

17. The system of claim 11 wherein the first actuator comprises a piezoelectric-stack.

18. The system of claim 11 wherein the second actuator comprises a piezoelectric-stack.

19. The system of claim 11 wherein the pin comprises an optical fiber.

20. The system of claim 11 further comprising a light sensor coupled to the pin for measuring the intensity of light transmitted through the pin.

21. The system of claim 20 wherein the light intensity measured by the light sensor provides an indication of the position of the pin in the bore.

22. The system of claim 20 wherein the light intensity measured by the light sensor provides an indication of the size of the dispensed liquid material.

23. The system of claim 11 further comprising a light sensor coupled to the pin, wherein the light sensor comprises a beam splitter, a light source, a first photodetector for detecting light transmitted from the light source and reflected from the beam splitter and a second photodetector for detecting light from the pin and reflected from the beam splitter.

24. The system of claim 11 further comprising a means for indicating a position of the pin in the bore, the means coupled to the pin.

25. The system of claim 11 further comprising a means for indicating the size of the dispensed liquid material, the means coupled to the pin.

26. A liquid delivery system comprising:
a positioning stage;
a liquid delivery apparatus coupled to the positioning stage to move the liquid delivery apparatus in one or more dimensions, the liquid delivery apparatus comprising:
a housing including a bore,
a pin including a tip, the pin movably disposed within the bore,
a reservoir including a port with an opening adjacent a side of the bore, the reservoir for holding a liquid material for delivery to the opening,
a first actuator coupled to the reservoir to dispense a metered amount of the liquid material from the reservoir to the opening, and
a second actuator coupled to the pin providing controlled movement of the pin within the bore, including movement of the tip past the opening to adhere dispensed liquid material to the tip, the second actuator also providing controlled vibration of the pin to separate the dispensed liquid material from the tip of the pin at a determined position; and a controller coupled to the liquid delivery apparatus, the controller including a memory for storing operating instructions and operative to:

move the pin toward a target area, cause the metered amount of liquid material to adhere to a tip of the pin as the pin moves toward the target area, sense when the tip of the pin is approximately a predetermined distance above the target area, and vibrate the pin to separate the liquid material onto the target area.

27. The system of claim 26 wherein the controller includes instructions that when executed cause the controller to sense an optical signal transmitted through the pin to determine a position of the bore.

28. The system of claim 26 wherein the controller includes instructions that when executed cause the controller to horizontally position the pin over the target area.

29. The system of claim 26 wherein the controller includes instructions that when executed cause the controller to vertically position the pin over the target area.

30. The system of claim 26 wherein the controller includes instructions that when executed cause the controller to compare a detected light signal transmitted through the pin with an expected light intensity to determine whether the liquid sample is adhered to the tip of the pin.

31. The system of claim 26 wherein the positioning stage comprises a coarse positioning stage and a fine positioning stage.

32. The system of claim 31 wherein the coarse positioning stage comprises a robotic device.

33. The system of claim 31 wherein the fine positioning stage comprises a horizontal microstage and a vertical microstage.

34. The system of claim 33 wherein each microstage comprises a piezoelectric-stack.

35. The system of claim 31 wherein the fine positioning stages further comprises a vibration control stage.

36. The system of claim 26 wherein the first actuator comprises a piezoelectric-stack.

37. The system of claim 26 wherein the second actuator comprises a piezoelectric-stack.

38. The system of claim 26 wherein the pin comprises an optical fiber.

39. The system of claim 26 further comprising a light sensor coupled to the pin, wherein during operation the light sensor measures light intensity transmitted through the pin.

40. The system of claim 26 wherein the light intensity measured by the light sensor provides an indication of the position of the pin in the bore.

41. The system of claim 26 further comprising a light sensor coupled to the pin, wherein the light sensor comprises a beam splitter, a light source, and a first and second photodetector, wherein during operation the first photodetector detects light transmitted from the light source and reflected from the beam splitter and the second photodetector detects light from the pin and reflected from the beam splitter.

42. The system of claim 26 further comprising a means for indicating a position of the pin in the bore, the means coupled to the pin.

43. The system of claim 26 further comprising a means for indicating the size of the dispensed liquid material.

* * * * *